(12) United States Patent
Taylor, Jr. et al.

(10) Patent No.: US 8,443,680 B2
(45) Date of Patent: May 21, 2013

(54) PIPE REEL LOAD SIMULATOR

(75) Inventors: Leland Harris Taylor, Jr., Houston, TX (US); Luca Suschitz, Houston, TX (US)

(73) Assignee: J. Ray McDermott, S.A., Houston, TX (US)

(*) Notice: Subject to any disclaimer, the term of this patent is extended or adjusted under 35 U.S.C. 154(b) by 97 days.

(21) Appl. No.: 13/181,690

(22) Filed: Jul. 13, 2011

(65) Prior Publication Data

US 2013/0014590 A1    Jan. 17, 2013

(51) Int. Cl.
*G01N 3/02* (2006.01)
*G01N 3/20* (2006.01)

(52) U.S. Cl.
USPC .............................. 73/849; 73/856

(58) Field of Classification Search
USPC ................................... 73/849, 856
See application file for complete search history.

(56) References Cited

U.S. PATENT DOCUMENTS

| | | | | |
|---|---|---|---|---|
| 4,260,287 A | * | 4/1981 | Uyeda et al. | 405/168.3 |
| 4,403,499 A | * | 9/1983 | Sack et al. | 73/7 |
| 5,503,024 A | * | 4/1996 | Bechtel et al. | 73/852 |

* cited by examiner

*Primary Examiner* — Lisa Caputo
*Assistant Examiner* — Jonathan Dunlap
(74) *Attorney, Agent, or Firm* — D. Neil LaHaye

(57) ABSTRACT

An arrangement of elements which are used to restrain and deflect a pipe specimen to a prescribed form with precisely controlled loads. A rigid frame includes a movable pipe bending form to which one end of a pipe specimen is connected and a rotating table to which the second end of the pipe specimen is connected. Means for assessing the drive torque used to draw the pipe specimen over the pipe bending form is provided in the form of a load cell. The rotating table is used in combination with a travelling pipe end truck foundation to generate a bending moment in the pipe specimen in the same plane as the pipe specimen is being bent by the pipe bending form. By the use of precise loads on the pipe specimen, computer analysis of the simulated reeling of the given pipe construction will produce predictions of the reeling tension, shear, and bending moment in the pipe at the point of the travelling pipe end as this point on the pipe approaches contact with the reel.

13 Claims, 6 Drawing Sheets

PIPE REEL LOAD SIMULATOR

FIELD AND BACKGROUND OF INVENTION

The invention is generally related to the reeling of pipe and more particularly to a pipe reel load simulator.

Heretofore, there have been limited means to test the behavior of a given steel pipe line construction assembly during the pipe reeling process. Assemblies to be tested are generally joints of pipe joined by butt welding of either a single carbon steel pipe with or without some sort of elastomeric coating, or such a carbon steel pipe which is also clad internally with a corrosion resistant alloy (CRA) or a dual wall pipe assembly known as "pipe in pipe". The means of testing specimens of these types of pipe line construction to confirm their suitability for installation by the pipe reeling process has involved simple bending tests whereby the pipe assembly specimen is either:

- bent over a steel form by applying a simple shear load at the free end of the specimen, thereby causing the specimen fixed at the base of the form to be pulled into conformance with the form;
- bent over a steel form by applying a simple shear load on each of the ends of the specimen; or
- bent using either a simple 3-point or 4-point opposing shear load condition.

Full scale tests can be performed using an actual pipe reeling vessel. However, such full scale tests require large amounts of specimen pipe as well as the time of costly operations of the specialized vessels used in the reeled pipeline construction business.

The reeling of steel pipe constructions involves straining the steel wall of the pipe into the plastic region. The analytical and numerical methods currently used to predict the behavior and residual integrity of a pipe construction which is reeled into its plastic limits are approximations. This is because the plastic behavior of the pipe construction during reeling is governed by the collective effects of actual material properties, precise material dimensions, and boundary loading conditions which are difficult to accurately model numerically or analytically.

In any structure loaded within its linear (non plastic) limit, the strain status is independent of the path and sequence of loading. In any nonlinear plasticity problem the status of stress and strain is highly dependent on the path and sequence of deformation patterns used to reach the status of interest. Thus, the application sequence of loads to the structure is influenced by the behavior when strained to the plastic limit.

For a physical test to provide meaningful results, the testing device must replicate as precisely as possible the actual working conditions for which the test is conceived. The current art of testing pipe construction exposed to pipe reeling strains does not accurately replicate the axial tension and the bending moment and shear loads which actually occur during the pipe reeling process. The inaccurate representation of the actual loading conditions can result in false test positives in pipe construction performance. The false test positives result in unpredicted failures during the execution of reeled pipe line construction projects, resulting in schedule delays, commercial, and possibly physical damage.

Therefore, it can be seen there is a need for a testing device that closely emulates the actual industrial process of reeling pipe to allow the validation of the designs of pipe line construction to be reeled.

SUMMARY OF INVENTION

The present invention addresses the above need and is drawn to an arrangement of elements which are used to restrain and deflect a pipe specimen to a prescribed form with precisely controlled loads. A rigid frame includes a movable pipe bending form to which one end of a pipe specimen is connected and a rotating table to which the second end of the pipe specimen is connected. Means for assessing the drive torque used to draw the pipe specimen over the pipe bending form is provided in the form of a load cell. The rotating table is used in combination with a travelling pipe end truck foundation to generate a bending moment in the pipe specimen in the same plane as the pipe specimen is being bent by the pipe bending form. Computer analysis of the simulated reeling of the given pipe construction will produce predictions of the reeling tension, shear, and bending moment in the pipe at the point of the travelling pipe end as this point on the pipe approaches contact with the reel. These predicted tensions, shears and bending moments can then be applied to the specimen by the invention and the behavior of the specimen under these conditions observed, measured, and compared to the computer analysis.

The various features of novelty which characterize the invention are pointed out with particularity in the claims annexed to and forming part of this disclosure. For a better understanding of the present invention, and the operating advantages attained by its use, reference is made to the accompanying drawings and descriptive matter, forming a part of this disclosure, in which a preferred embodiment of the invention is illustrated.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

Figure 1:
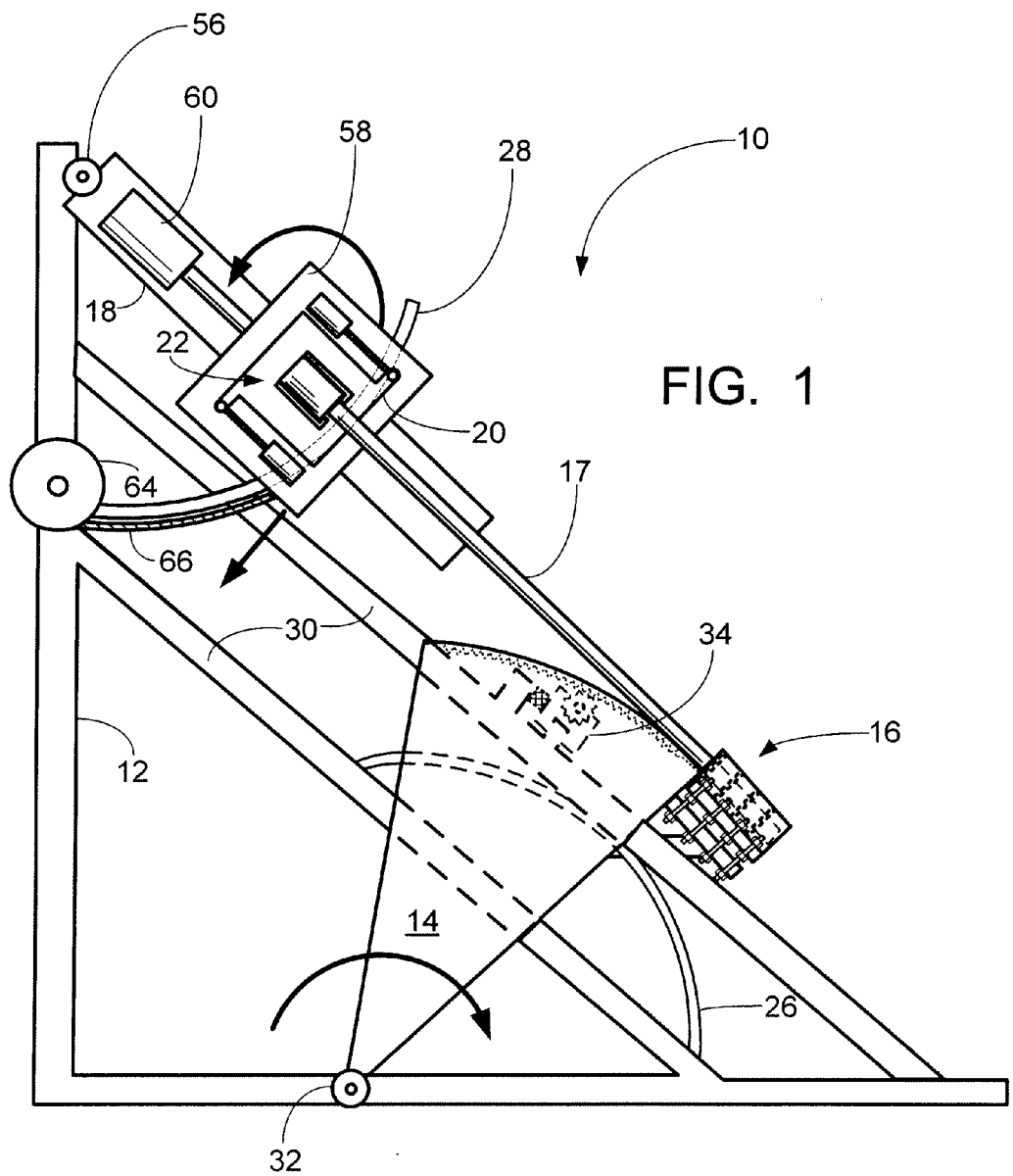
FIG. 1 is a schematic illustration of the invention.
Figure 2:
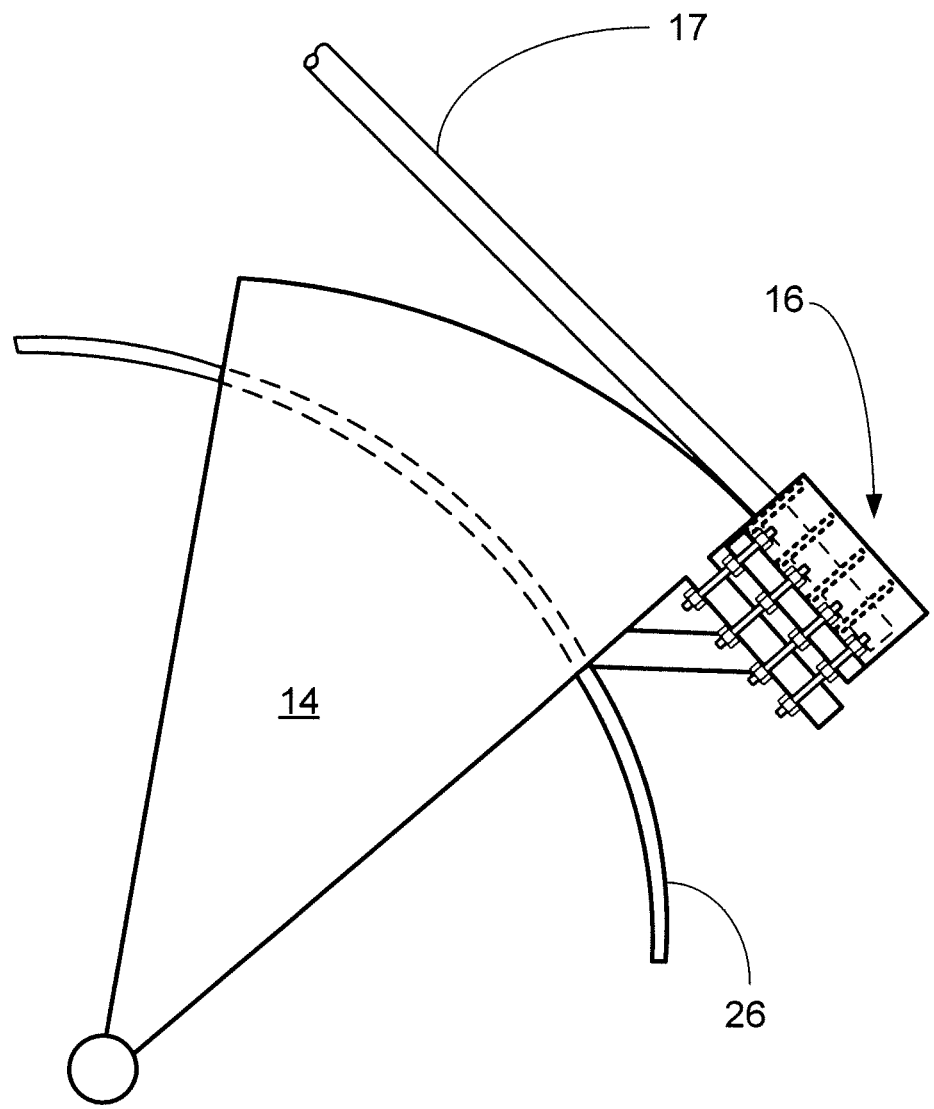
FIG. 2 is a more detailed view of the pipe bending form.
Figure 3:
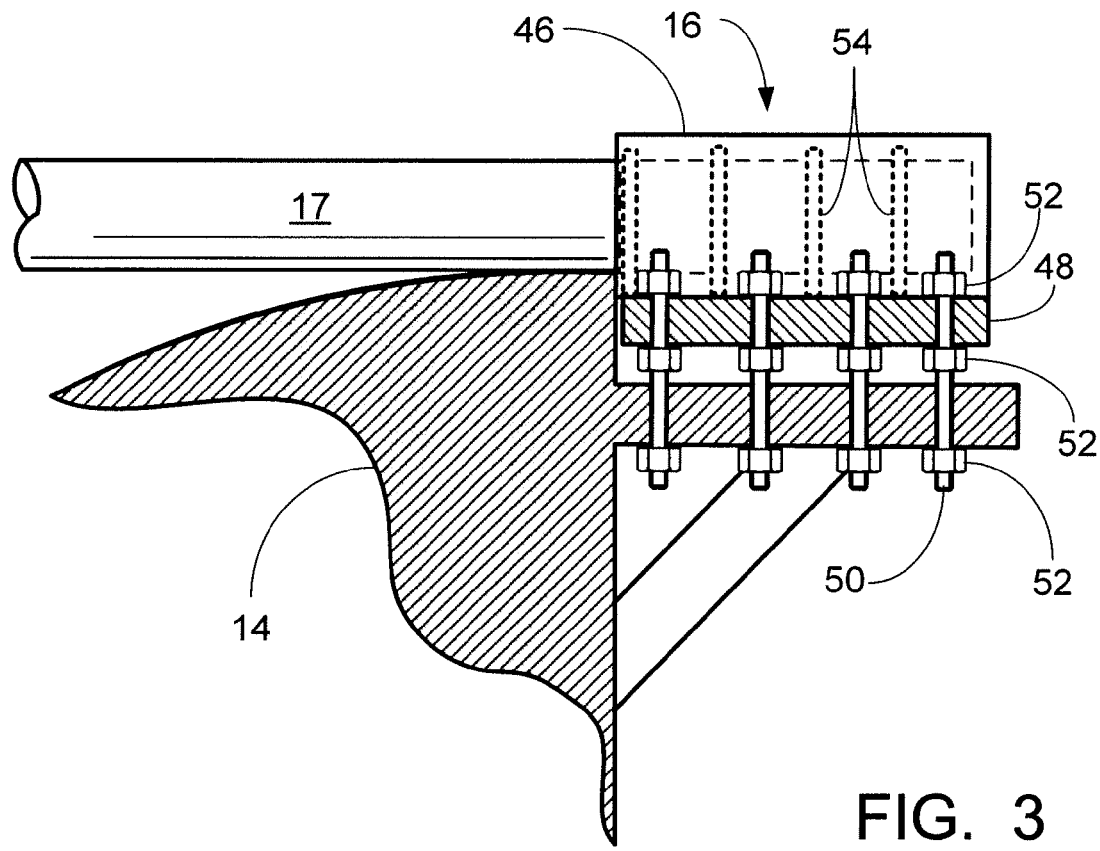
FIGS. 3 and 4 are detail views of the means of attaching the pipe to the pipe bending form.
Figure 4:
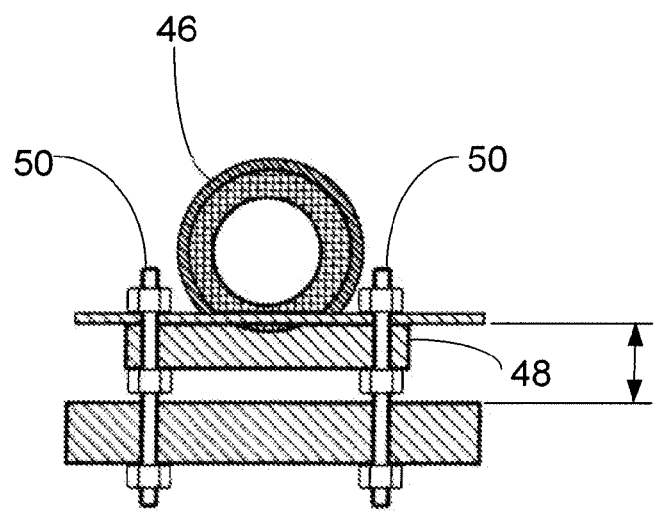

As seen in FIG. 1, the pipe reeling load simulator 10 is generally comprised of a rigid frame 12, a pipe bending form 14, means 16 and 22 for securing each end of a pipe 17 during bending operations, a beam 18, a table 20, and means 24 for determining the driving torque used to draw the pipe 17 over the pipe bending form 14.

Rigid frame 12 is formed from any suitable material such as steel, is L-shaped in the embodiment shown and may include one or more cross braces 30. Two are shown in this embodiment. The number of cross braces will depend on the size of the pipe specimen to be bent and the leverage required for bending the pipe. While an L-shaped frame is shown it should be understood that other suitable shapes may be used.

Pipe bending form 12 is essentially pie shaped with the narrow end pivotally mounted, indicated by numeral 32, to one leg of rigid frame 12. To provide for consistent movement of the pipe bending form 12 during operation, an arched guide track 26 is attached between the cross braces 30. Pipe bending form 12 is engaged with the guide track 26 for movement thereon by any suitable means such as rollers not shown.

Figure 6:
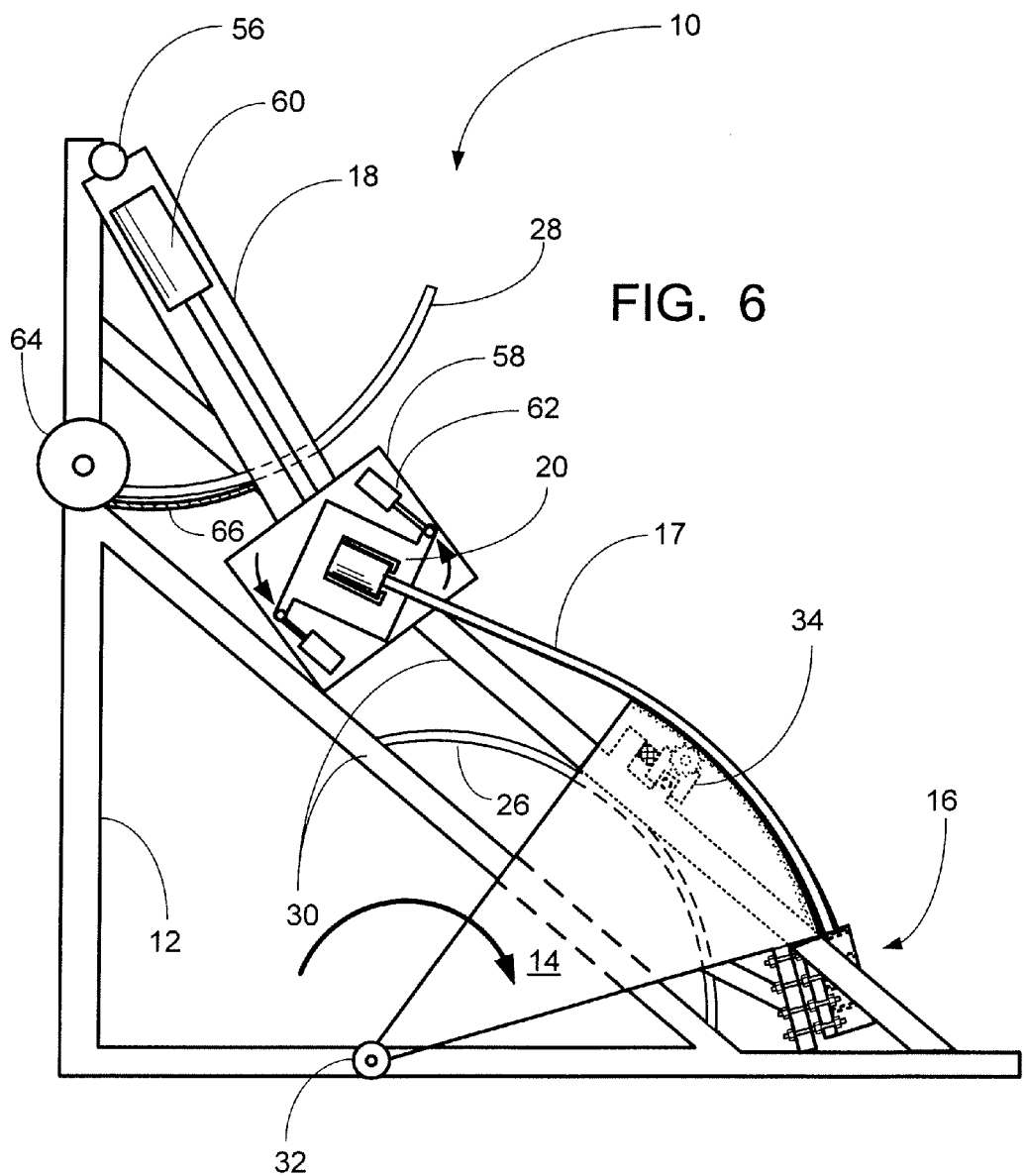
FIG. 6 illustrates the invention after a pipe specimen has been bent.
Figure 7:
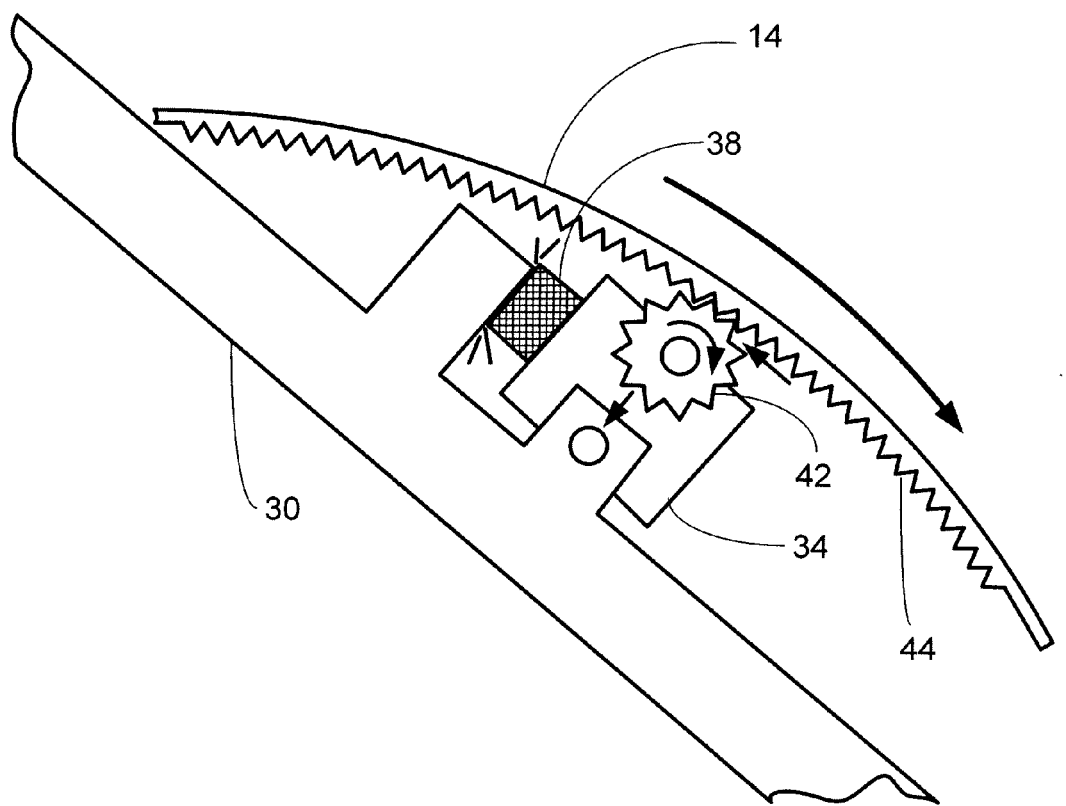
FIG. 7 is a detail view of the engagement between the motor drive and the pipe bending form.

As seen in FIGS. 1, 6, and the detail view of FIG. 7, a motor drive 34 is mounted on a cross brace 30 and has a driving gear 42 engaged with gears 44 on the pipe bending form 12. The motor drive 34 is preferably mounted on a pin 36 that retains the motor drive 34 in position on the cross brace 30 but allows a limited range of rotation on the pin 36. Motor drive 34 drives the pipe bending form 12 during operations to cause bending of the pipe 17 over the arched end of the pipe bending form 12.

Means for determining the driving torque used to draw the pipe specimen 17 over the pipe bending form 12 is provided in the form of a load cell 38 mounted on either the motor drive 34 or a tab 40 on the cross brace 30 adjacent the motor drive 34 such that the load cell 38 is between them and the rotational force of the motor drive 34 during pipe bending operation puts pressure on the load cell 38 between the motor drive 34 and tab 40.

Means 16 and 22 for securing each end of the pipe 17 during bending operations are each comprised of a receptacle 46 with a flange plate 48 for mounting to either the pipe bending form 12 or the table 20. Studs 50 and nuts 52 are used to secure the receptacle 46 on the pipe bending form 12 and the table 20. The studs and nuts allow height adjustment as required. Centralizer rings 54 are used to properly center the pipe 17 in the receptacle 46.

The beam 18 is pivotally mounted, indicated by numeral 56, on the rigid frame 12 and located so as to be spaced apart from the pivotal mount 32 of the pipe bending form 14. A truck 58 is mounted on the beam 18 for selective movement along the length of the beam 18. The table 20, referenced above, is mounted on the truck 48 so as to be rotatable thereon. Means 22 for securing one end of the pipe is mounted on the table 20.

Figure 5:
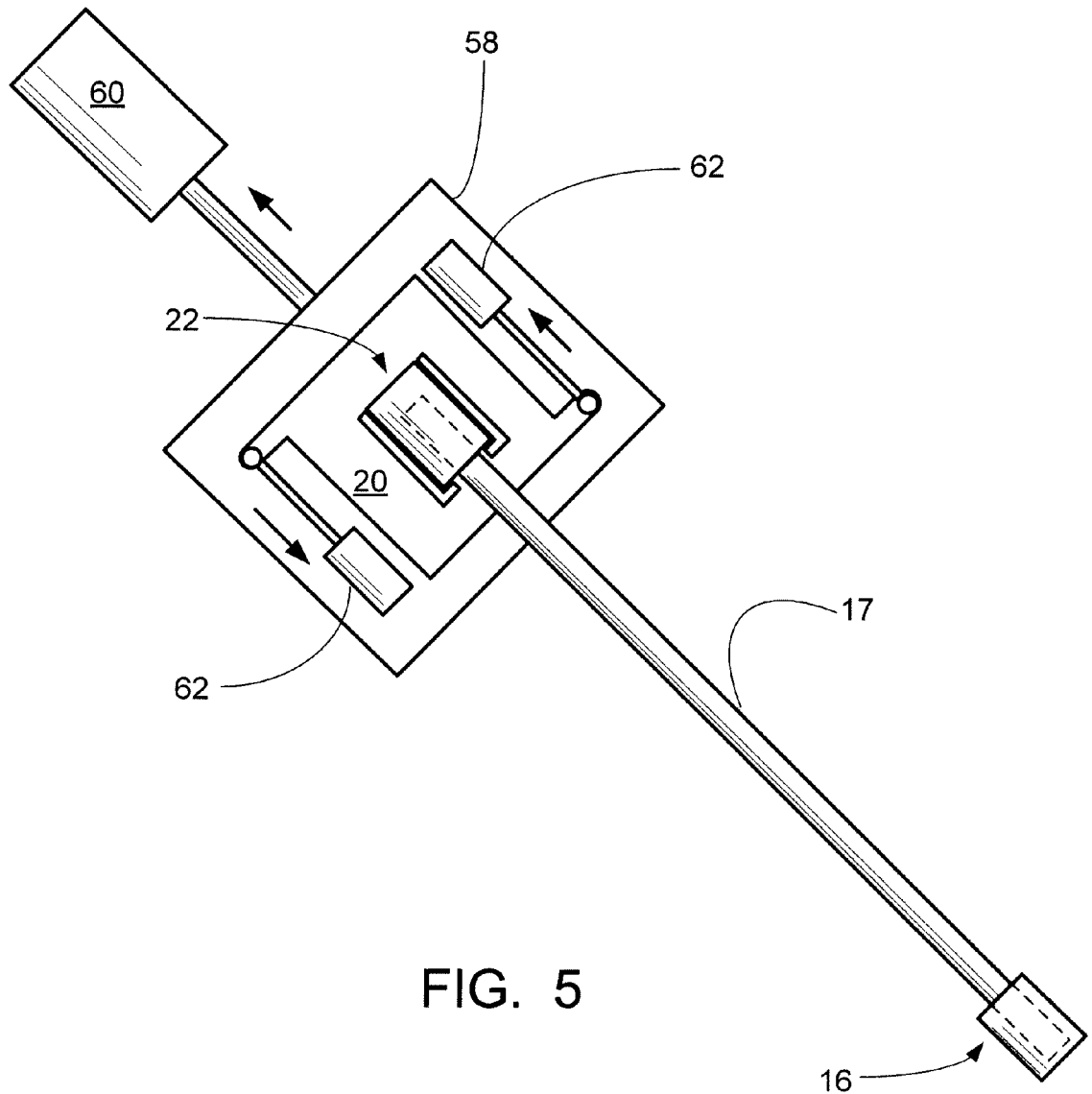
FIG. 5 is a detail view that illustrates the portion of the invention at the travelling end of the pipe.

The truck 58 is selectively moved along the beam 18 by means of cylinder and piston 60, seen in FIGS. 1 and 5-6. The cylinder & piston 60 are mounted in place on the beam 18 and attached to the truck 58 for selective movement of the truck 58 and the table 20 mounted on the truck 58.

As seen in FIGS. 1 and 5-6, hydraulic pistons and cylinders 62 mounted in place on the truck 58 are attached on opposite sides of the table 20 for applying bending couple to the table 20 and pipe 17 engaged therewith via connection means 22.

Draw works 64 is mounted on the frame 12 and has a line 66 connected between the draw works 64 and beam 18 for moving the beam 18 and its associated equipment during operations. The beam 18 is movably mounted on guide track 28. The draw works 64, line 66, and guide track 28 are an example of one means of causing movement of the beam 18. Other structural arrangements may be used.

In operation, a pipe specimen 17 has each end inserted into receptacles 16 and 22. The receptacles are then respectively mounted on the pipe bending form 14 and the table 20 and the height adjusted. The motor drive 34 is used to rotate the pipe bending form 14 in the direction indicated by the arrow in FIG. 1 to cause bending of the pipe 17 over the pipe bending form 14. During this bending motion the cylinder and piston 60 and the draw works 64 and line 66 are used to cause the beam 18 to move along guide track 28 and rotate in the direction indicated by the arrow in FIG. 1 while the hydraulic cylinder/pistons 62 on the truck 58 are used to rotate the table 20 and apply a bending couple to the table 20 and pipe 17. These movements are all known forces. As seen in FIG. 7, the load cell 38 is used to determine the drive torque required to bend the pipe 17 as a result of the reaction of the motor drive 34.

The invention provides several advantages over the previously used means of test bending pipe.

The torque used to reel the pipe can be readily calculated.

The creation of a bending couple on the end of the pipe that would not immediately be contacting a pipe reel adds a bending element missing in previously used testing apparatus.

The creation of a precise bending couple and axial tension in the pipe specimen during reeling will allow the observation of the behavior of the pipe construction under simulated industrial loads to eliminate or greatly reduce false positives for the ability to bend a given pipe construction onto a reel.

While specific embodiments and/or details of the invention have been shown and described above to illustrate the application of the principles of the invention, it is understood that this invention may be embodied as more fully described in the claims, or as otherwise known by those skilled in the art (including any and all equivalents), without departing from such principles.

What is claimed as invention is:

1. A pipe reeling load simulator for bending a pipe specimen having first and second ends, comprising:
   a. a rigid frame;
   b. a pipe bending form pivotally mounted on the rigid frame;
   c. means for connecting the first end of the pipe specimen to the pipe bending form;
   d. a beam pivotally attached to the rigid frame at a separate location from the pipe bending form;
   e. means for selectively causing movement of the beam;
   f. a table mounted on the beam for rotational and translational movement on the beam;
   g. means for connecting the second end of the pipe specimen to the table;
   h. means for driving the pipe bending form; and
   i. means for determining the driving torque used to draw the pipe specimen over the pipe bending form.

2. The pipe reeling load simulator of claim 1, wherein the means for determining the driving torque comprises a load cell engaged with the means for driving the pipe bending form.

3. The pipe reeling load simulator of claim 1, further comprising a first guide track attached to the rigid frame on which the pipe bending form moves.

4. The pipe reeling load simulator of claim 1, further comprising a second guide track attached to the rigid frame on which the beam moves.

5. The pipe reeling load simulator of claim 1, wherein the table is rotatably mounted on a truck that is movably mounted on the beam for translational movement thereon.

6. The pipe reeling load simulator of claim 5, further comprising means for selectively causing rotational movement of the table.

7. A pipe reeling load simulator for bending a pipe specimen having first and second ends, comprising:
   a. a rigid frame;
   b. a pipe bending form pivotally mounted on the rigid frame;
   c. means for connecting the first end of the pipe specimen to the pipe bending form;
   d. a beam pivotally attached to the rigid frame at a separate location from the pipe bending form;
   e. means for selectively causing movement of the beam;
   f. a table mounted on the beam for rotational and translational movement on the beam;
   g. means for selectively causing rotational and translational movement of the table;

h. means for connecting the second end of the pipe specimen to the table;
i. means for driving the pipe bending form; and
j. a load cell engaged with the means for driving the pipe bending form for determining the driving torque used to draw the pipe specimen over the pipe bending form.

8. The pipe reeling load simulator of claim 7, further comprising a first guide track attached to the rigid frame on which the pipe bending form moves.

9. The pipe reeling load simulator of claim 7, further comprising a second guide track attached to the rigid frame on which the beam moves.

10. The pipe reeling load simulator of claim 7, wherein the table is rotatably mounted on a truck that is movably mounted on the beam for translational movement thereon.

11. A pipe reeling load simulator for bending a pipe specimen having first and second ends, comprising:
  a. a rigid frame;
  b. a pipe bending form pivotally mounted on the rigid frame;
  c. means for connecting the first end of the pipe specimen to the pipe bending form;
  d. a beam pivotally attached to the rigid frame at a separate location from the pipe bending form;
  e. means for selectively causing movement of the beam;
  f. a truck mounted on the beam for translational movement thereon;
  g. means for selectively causing translational movement of the truck on the beam;
  h. a table mounted on the truck for rotational movement thereon;
  i. means for selectively causing rotational movement of the table;
  j. means for connecting the second end of the pipe specimen to the table;
  k. means for driving the pipe bending form; and
  l. a load cell engaged with the means for driving the pipe bending form for determining the driving torque used to draw the pipe specimen over the pipe bending form.

12. The pipe reeling load simulator of claim 11, further comprising a first guide track attached to the rigid frame on which the pipe bending form moves.

13. The pipe reeling load simulator of claim 11, further comprising a second guide track attached to the rigid frame on which the beam moves.

* * * * *